United States Patent
Bigorra et al.

(10) Patent No.: US 6,432,895 B1
(45) Date of Patent: Aug. 13, 2002

(54) DETERGENT MIXTURES CONTAINING OLIGOMERIC ESTERQUATS

(75) Inventors: Joaquin Bigorra, Sabadell; Nuria Bonastre Gilabert, Barberá del Vallés; Rafael Pi Subirana, Granollers, all of (ES)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/529,067

(22) PCT Filed: Sep. 25, 1998

(86) PCT No.: PCT/EP98/06115

§ 371 (c)(1),
(2), (4) Date: Jun. 23, 2000

(87) PCT Pub. No.: WO99/18178

PCT Pub. Date: Apr. 15, 1999

(30) Foreign Application Priority Data

Oct. 6, 1997 (DE) .......................................... 197 43 687

(51) Int. Cl.$^7$ .............................. C11D 1/62; C11D 3/32
(52) U.S. Cl. ...................... 510/123; 510/119; 510/501; 510/504
(58) Field of Search ................................ 510/119, 123, 510/504, 501

(56) References Cited

U.S. PATENT DOCUMENTS

| | | | |
|---|---|---|---|
| 4,172,887 A | 10/1979 | Vanlerberghe et al. | 424/70 |
| 5,349,106 A | 9/1994 | Behler et al. | 564/282 |
| 5,670,677 A | 9/1997 | Ponsati Obiols et al. | 554/114 |
| 5,869,716 A | 2/1999 | Pi Subirana et al. | 554/114 |
| 5,880,299 A | 3/1999 | Ponsati Obiols et al. | 554/109 |

FOREIGN PATENT DOCUMENTS

| | | |
|---|---|---|
| DE | 20 24 051 | 10/1979 |
| DE | 40 26 184 | 2/1992 |
| DE | 1 165 574 | 3/1994 |
| DE | 43 08 792 | 4/1994 |
| DE | 44 09 322 | 4/1995 |
| DE | 195 39 846 | 11/1996 |
| DE | 19539846 | * 11/1996 |
| EP | 0 634 475 | 1/1995 |
| EP | 634475 | * 1/1995 |
| FR | 2 252 840 | 8/1975 |
| GB | 1 333 475 | 10/1973 |
| GB | 926919 | 7/1994 |
| WO | WO91/01295 | 2/1991 |
| WO | WO98/41604 | 9/1998 |

OTHER PUBLICATIONS

Puchta, et al., Tenside Surf. Det., 30, (1993), pp. 186–191.
Brock, Tenside Surf. Det., 30, (1993), pp. 394, 396 & 398.
Lagerman, et al., JAOCS, 71, (Jan., 1994), pp. 97–100.
Shapiro, et al., Cosmetics & Toiletries, 109, Dec., 1994, pp. 77, 78 & 80.
J. Falbe (ed.), Surfactants in Consumer Products, Springer Verlag, Berlin, (1987), pp. 54–124.
J. Falbe (ed.), Katalysatoren, Tenside und Mineraloeladditive (Catalysts, Surfactants and Mineral Oil Additives), Thieme Verlag, Stuttgart, (1978), pp. 123–217.
"Kosmetische Faerbemittel", Farbstoffkommission der Deutschen Forschungsgemeinschaft, Verlag Chemie, Weinheim, (1984), pp. 81–106.

* cited by examiner

Primary Examiner—Charles Boyer
(74) Attorney, Agent, or Firm—John E. Drach; Henry E. Millson, Jr.

(57) ABSTRACT

Detergent mixtures comprising (a) an oligomeric esterquat which is the product of the process which comprises reacting a mixture of a mono-carboxylic acid and a dicarboxylic acid with an alkanolamine to form an alkanolamine oligoester and reacting the alkanolamine oligoester with an alkylating agent and (b) the product of the process which comprises reacting an alkylene oxide and a fatty acid amidoamine, wherein the weight ratio of components (a) to (b) is from about 10:90 to about 90:10; and wherein the oligomeric esterquat has at least two cationic centers.

12 Claims, No Drawings

DETERGENT MIXTURES CONTAINING OLIGOMERIC ESTERQUATS

BACKGROUND OF THE INVENTION

1. Field of the Invention

This invention relates to detergent mixtures containing oligomeric esterquats and alkoxylated fatty acid amidoamines and to the use of the mixtures for the production of fabric softeners and hair-care compositions.

2. Statement of Related Art

As a result of increased biodegradability requirements, quaternary fatty acid alkanolamine ester salts, so-called "esterquats", have displaced tetraalkyl ammonium compounds as cationic surfactants both for the production of fabric softeners and for the conditioning of hair. Overviews on this subject have been published, for example, by R. Puchta et al. in Tens. Surf. Det., 30, 186 (1993), by M. Brock in Tens. Surf. Det. 30, 394 (1993), by R. Lagerman et al. in J. Am. Oil. Chem. Soc., 71, 97 (1994) and by l. Shapiro in Cosm. Toil. 109, 77 (1994). However, there is a demand on the market for products with further improved properties.

Accordingly, the complex problem addressed by the present invention was to provide detergent mixtures which would have improved conditioning and antistatic properties and complete biological degradability, could be dissolved quickly and completely, even in cold water, would have a sufficiently high viscosity but would not thicken or form gels in storage and, finally, would dissolve clearly in any ratio with water without any need for alcohols.

DESCRIPTION OF THE INVENTION

The present invention relates to detergent mixtures containing (a) oligomeric esterquats obtainable by condensation of mixtures of mono-and dicarboxylic acids with alkanolamines and subsequent quaternization of the alkanolamine oligoesters and (b) products of the addition of alkylene oxides onto fatty acid amidoamines.

It has surprisingly been found that the mixtures according to the invention not only are highly concentrated and water-clear, they also have an advantageously high and stable viscosity. The preparations can be diluted with water in any quantities and may then be immediately used as fabric softeners or hair-care compositions. They provide both synthetic and natural fibers with a particularly pleasant soft feel and, in addition, reduce the static charging between the fiber filaments to a quite considerable extent. Another advantage is that they can be dispersed particularly easily in cold water and, in addition, are readily biodegradable.

Oligomeric esterguats

The oligomeric esterquats have at least two cationic centers and, accordingly, differ from other known esterquats which have only one quaternary nitrogen. The production and use of these substances is known from DE-C1 19539846 (Henkel). In simple terms, the synthesis principle consists in linking several, but preferably exactly two, polyfunctional alkanolamines by means of a dicarboxylic acid, completely or partly esterifying the free hydroxyl groups with monocarboxylic acids and then quaternizing the nitrogen atoms present in the oligomeric or dimeric ester by methods known per se.

Typical examples of monocarboxylic acids, which may be used as one of the two acid components of the oligomeric esterquats, are fatty acids and oxocarboxylic acids containing 6 to 22 carbon atoms such as, for example, caproic acid, caprylic acid, 2-ethyl hexanoic acid, capric acid, lauric acid, isotridecanoicacid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example coconut, palm, palm kernel or tallow acid, preferably in hydrogenated or partly hydrogenated form, are preferred. Examples of suitable dicarboxylic acids, which may be used as a second bridging carboxylic acid component, are succinic acid, maleic acid, glutaric acid, 1,12-dodecanedioic acid and, more particularly, adipic acid. Oligomeric esterquats based on fatty acids containing 6 to 22 carbon atoms and adipic acid are preferably used. To produce the oligomeric esterquats, the mono-and dicarboxylic acids may be used in a molar ratio of 1:1 to 3:1 and preferably 1.5:1 to 2.5:1.

The alkanolamine component of the oligomeric esterquats may be derived from methyl diethanolamine, but is preferably derived from tri-ethanolamine and from mixtures of the two. To produce the compounds, the mono-/dicarboxylic acids on the one hand and the alkanolamines on the other hand may be used in a molar ratio of 1:1 to 3:1 and are preferably used in a molar ratio of 1.5:1 to 2:1.

The esterification may be carried out in known manner, as described for example in International patent application WO 91101295 (Henkel). The esterification is advantageously carried out at temperatures of 120 to 220° C. and, more particularly, 130 to 170° C. and under pressures of 0.01 to 1 bar. Suitable catalysts are hypophosphorous acid and alkali metal salts thereof, preferably sodium hypophosphite, which may be used in quantities of 0.01 to 0.1% by weight and are preferably used in quantities of 0.05 to 0.07% by weight, based on the starting materials. In the interests of particularly high color quality and stability, it has proved to be of advantage to use alkali metal and/or alkaline earth metal borohydrides such as, for example, potassium, magnesium and in particular sodium borohydride. The co-catalysts are normally used in quantities of 50 to 1000 ppm and more particularly 100 to 500 ppm, again based on the starting materials. Corresponding processes are also the subject of German patents DE-C1 4308792 and DE-C1 4409322 (Henkel), to which reference is specifically made here. Mixtures of the fatty acids and dicarboxylic acids may be used or the esterification may be carried out with the two components in succession.

The quaternization of the fatty acid/dicarboxylic acid alkanolamine esters may be carried out in known manner. Although the reaction with the alkylating agents can be carried out in the absence of solvents, it is advisable to use at least small quantities of water or lower alcohols, preferably isopropyl alcohol, for the preparation of concentrates which have a solids content of at least 80% by weight and, more particularly, at least 90% by weight. Suitable alkylating agents are alkyl halides, for example methyl chloride; dialkyl sulfates, for example dimethyl sulfate or diethyl sulfate; or dialkyl carbonates such as, for example, dimethyl carbonate or diethyl carbonate. The esters and the alkylating agents are normally used in a molar ratio of 1:0.95 to 1:1.05, i.e. in a substantially stoichiometric ratio. The reaction temperature is normally in the range from 40 to 80° C. and more particularly in the range from 50 to 60° C. After the reaction, it is advisable to destroy unreacted alkylating agent by addition of, for example, ammonia, an (alkanol)amine, an amino acid or an oligopeptide, as described for example in German patent application DE-A1 4026184 (Henkel).

In the reaction of the alkanolamines with the mixtures of mono-and dicarboxylic acids, complex mixtures predominantly containing dimers, i.e. species in which two alkanolamines are bridged by a dicarboxylic acid and of which the free hydroxyl groups are partly esterified with monocarboxylic acids, are obtained. According to gel permeation chromatography, the mixtures also contain oligomeric esters where 3 to 4 quaternary centers are present. Monomeric compounds containing only one quaternary nitrogen are undesirable for performance-related reasons because they adversely affect clear solubility. Although they cannot be completely prevented from occurring, their content can be reduced to below 5% by weight through the presence of a sufficient quantity of dicarboxylic acid. The dimeric compounds corresponding to formula (I):

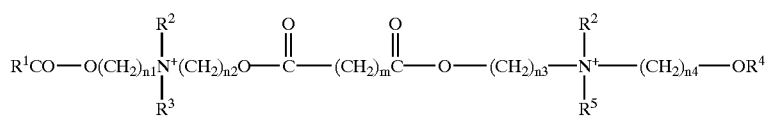

(I)

in which $R^1CO$ is an aliphatic, linear or branched, saturated or unsaturated acyl group containing 6 to 22 corbon atome, $R^2$ is an alkyl group containing 1 to 4 carbon atoms, $R^3$ and $R^5$ independently of one nother represent alkyl or hydroxyalkyl groups containing 1 to 4 carbon atoms, $R^4$ is hydrogen or has the same meaning as $R^1$ CO, n1, n2, n3 and n4 independently of one another have a value of 1 to 5 and m has a value of 1 to 10. Dimeric esterquats with particularly advantageous properties correspond to formula (I) where $R^1CO$ is a linear saturated acyl group containing 12 to 18 carbon atoms, $R^2$ is a methyl group, $R^3$ and $R^5$ each represent hydroxyethyl groups, $R^4$ has the same meaning as $R^1$ CO n1, n2, n3 and n4 each have a value of 2 and m has a value of 4. The oligomeric esterquats preferably contain 20 to 90% by weight and more preferably 40 to 80% by weight of dimers, 10 to 80% by weight and more preferably 20 to 60% by weight of oligomers and less than 5% by weight of monomers, with the proviso that the quantities mentioned add up to 100% by weight.

Alkoxylated Fatty Acid Amidoamines

Alkoxylation products of fatty acid amidoamines are also known from the literature and preferably correspond to formula (II):

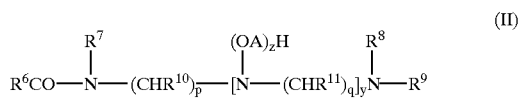

(II)

in which $R^6CO$ is an aliphatic, linear or branched, saturated or unsaturated. acyl group containing 6 to 22 carbon atoms, $R^7$ and $R^8$ independently of one another represent hydrogen or an optionally hydroxysubstituted alkyl group containing 1 to 4 carbon atoms, $R^9$ is hydrogen, an alkyl group containing 1 to 4 carbon atoms or has the same meaning as $R^6CO$, $R^{10}$ and $R^{11}$ independently of one another represent hydrogen or a methyl group, A is a linear or branched alkylene group containing 2 to 4 carbon atoms, p and q independently of one another have a value of 1 to 3, y has a value of 1 to 3 and z has a value of 1 to 20.

They are normally produced from dialkylenetriamines or trialkylene-tetramines which are first esterified with 1 to 2 moles of carboxylic acid and then reacted in known manner with alkylene oxides, preferably ethylene oxide, for insertion into the free NH bonds. Typical examples of suitable oligoamines are diethylenetriamine, dipropylenetriamine, triethylene-tetramine and tripropylenetetramine and mixtures thereof. Suitable car-boxylic acids are the fatty acids containing 6 to 22 carbon atoms such as, for example, caproic acid, caprylic acid, 2-ethyl hexanoic acid, capric acid, lauric acid, isotridecanoic acid, myristic acid, palmitic acid, paimitoleic acid, stearic acid, isostearic acid, oleic acid, elaidic acid, petroselic acid, linoleic acid, linolenic acid, elaeostearic acid, arachic acid, gadoleic acid, behenic acid and emucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example coconut, palm, palm kernel or tallow acid, preferably in hydrogenated or partly hydrogenated form, are preferred. It has proved to be of particular advantage to use the carboxylic acids in such quantities that, on average, diamides are obtained. In addition, alkoxylated fatty acid amidoamines corresponding to formula (II), where $R^6CO$ is a linear saturated acyl group containing 12 to 18 carbon atoms, $R^7$, $R^8$, $R^{10}$ and $R^{11}$ represent hydrogen, $R^9$ has the same meaning as $R^6CO$, A is an ethylene group, p and q each have a value of 2, y has a value of 1 and z has a vlaue of 5 to 10, are particularly preferred for applicational reasons.

The alkoxylation may be carried out in known manner, i.e. ethylene oxide, propylene oxide or mixtures thereof are added in the presence of acidic, but preferably basic catalysts, for example sodium methylate or calcined hydrotalcite. Nonionic compounds are formed, but are quickly protonated in acidic solution and then show pseudocationic behavior.

According to the invention, the detergent mixtures may contain components (a) and (b) in a ratio by weight of 10:90 to 90:10, preferably 25:75 to 75:25 and more preferably 40:60 to 60:40.

Commercial Applications

The present invention also relates to the use of the detergent mixtures for the production of fabric softeners and hair-care preparations in which they may be present in quantities of 1 to 50% by weight, preferably 5 to 35% by weight and more preferably 10 to 25% by weight. Apart from the possibility of directly using the mixtures for the stated purpose, the most simple form of use consists in diluting them with water to the required in-use concentration.

Surfactants

In this connection, other additives, more particularly other surfactants, which are compatible with components (a) and (b) may also be added to the preparations. The surfactants in question are, above all, other nonionic or cationic or amphoteric or zwitterionic surfactants. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysor-bates and amine oxides. If the nonionic surfactants contain polyglycol ether chains, they may have a conventional homolog distribution, although they preferably have a narrow-range homolog distribution. Typical examples of cationic surfactants are quaternary ammonium compounds and monomeric esterquats, more particularly quaternized fatty acid trialkanolamine ester salts. Typical examples of amphoteric or zwifterionic surfactants are alkylbetaines, alkylamidobetaines, amino-propionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineraldladditive (Catalysts, Surfactants and Mineral Oil Additives)", Thieme Verlag, Stuttgart, 1978, pages 123–217.

Auxiliaries and additives

Depending on the application envisaged, i.e. fabric softening or hair conditioning, the preparations obtainable using the detergent mixtures may contain other typical auxiliaries and additives, such as oil components, emulsifiers, superfatting agents, pearlizing waxes, stabilizers, consistency factors, thickeners, cationic polymers, silicone compounds, biogenic agents, antidandruff agents, film formers, preservatives, hydrotropes, solubilizers, UV filters, insect repellents, self-tanning agents, perfume oils, dyes and the like.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-22}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, ring opening products of epoxidized fatty acid esters with polyols, silicone oils and/or aliphatic or naphthenic hydrocarbons.

Suitable emulsifiers are, for example, nonionic surfactants from at least one of the following groups:
(1) products of the addition of 2 to 30 moles of ethylene oxide and/or 0 to 50 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;
(2) $C_{12/18}$ fatty acid monoesters and diesters of addition products of 1 to 30 moles of ethylene oxide onto glycerol;
(3) glycerol monoesters and diesters and sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) addition products of 15 to 60 moles of ethylene oxide onto castor oil and/or hydrogenated castor oil;
(6) polyol esters and, in particular, polyglycerol esters such as, for example, polyglycerol polyricinoleate, polyglycerol poly-12-hydroxy-istearate or polyglycerol dimerate. Mixtures of compounds from several of these classes: are also suitable;
(7) addition products of 2 to 15 moles of ethylene oxide onto castor oil and/or hydrogenated castor oil;
(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(9) mono-, di and trialkyl phosphates and mono-, di- and/or tri-PEG-alkyl phosphates;
(10) wool wax alcohols;
(11) polysiloxanelpolyalkyl polyether copolymers and corresponding derivatives;
(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and
(13) polyalkylene glycols.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. $C_{2/18}$ fatty acid monoesters and diesters of addition products of ethylene oxide onto glycerol are known as refatting agents for cosmetic formulations from DE-PS 20 24 051.

$C_{8/18}$ alkyl mono- and oligoglycosides, their production and their use as surfactants are known from the prior-art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example coconutalkyl dimethyl ammonium glycinate, N-acylaminopropyl-N,N-dimethyl ammonium glycinates, for example coconutacylaminopropyl dimethyl ammonium glycinate, and 2-alkyl-3- carboxymethyl-3-hydroxyethyl imidazolines containing 8 to 18 carbon atoms in the alkyl or acyl group and coconutacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coconut-alkylaminopropionate, cocoacylaminoethyl aminopropionate and $C_{12/18}$ acylsarcosine. According to the invention, other suitable emulsifiers besides ampholytic surfactants are quaternary emulsifiers, those of the esterquat type, preferably. methyl-quatemized difatty acid triethanolamine ester salts, being particularly preferred.

Superfaffing agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, particularly ethylene glycol distearate; fatty acid: alkanolamides, especially coconut acid diethanolamide; partial glycerides,: especially stearic acid monoglyceride; esters of polybasic, optionally hydroxysubstituted carboxylic acids with fatty alcohols containing 6 to 22 carbon atoms, especially long-chain esters of tartaric acid; fatty compounds, for example fatty alcohols, fatty ketones, fatty aldehydes, fatty ethers and fatty carbonates which contain a total of at least 24 carbon atoms, especially laurone and distearyl ether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups; and mixtures thereof.

The consistency factors mainly used are fatty alcohols containing 12 to 22 and preferably 16 to 18 carbon atoms and also partial glycerides. A combination of these substances with alkyl oligoglucosides and/or fatty acid-N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol mono-esters and diesters of fatty acids, polyacrylates (for example Carbopols® [Goodrichl] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethox-ylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quatemized vinyl pyrrolidone/vinyl imidazole polymers such as, for example, Luviquato (BASF), condensation products of polyglycols and amines, quatemized collagen polypeptides such as, for example, Lauryidimonium Hydroxypropyl Hydrolyzed Collagen (Lamequat®L/Grinau), quaternized wheat polypeptides, polyethyleneimine, cationic silicone polymers such as, for example, amodimethicone, copolymers of adipic acid and dimethylamino hydroxypropyl diethylenetriamine (Cartaretine®/Sandoz), copolymers of acrylic acid with dimethyl diallyl ammonium chloride (Merquat® 550/Chemviron), polyaminopolyamides as described, for example, in FR-A 2 252 840 and crosslinked water-soluble polymers thereof, cationic chitin derivatives such as, for example, quatemized chitosan, optionally in microcrystalline distribution, condensation products of dihaloalkys, for example dibromobutane, with bis-dialkylamines, for example bis-dimethylamino-1,3-propane, cationic guar gum such as, for example, Jaguar®CBS, Jaguar®C-17, Jaguar®C-16 of Celanese, USA, quatemized ammonium salt polymers such as, for example, Mirapol® A-15, Mirapol® AD-1, Mirapol® AZ-1 of Miranol, USA.

Suitable silicone compounds are, for example, dimethyl polysilox-anes, methylphenyl polysiloxanes, cyclic silicones and amino-, fatty acid-,alcohol-, polyether-, epoxy-, fluorine-, glycoside- and/or alkyl-modified silicone compounds which may be both liquid and resin-like at room temperature. Typical examples of fats are glycerides while suitable waxes are inter alia beeswax, camauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers. In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, proteolytic enzymes and, vitamin complexes. Suitable antidandruff agents are climbazol, octopirox and zinc pyrithione. Typical film formers are, for example, chitosan, microcrystalline chitosan, quatemized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases include montmorillonites, clay minerals, Pemulen and alkyl-modified Carbopol types (Goodrich).

UV filters in the context of the invention are, for example, organic substances which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor and derivatives thereof, for example 3-(4-methylbenzylideneycamphor;

4-aminobenzoic acid derivatives, preferably 4-(dimethylamino)-benzoic acid-2-ethylhexyl ester, 4-(dimethylamino)-benzoic acid-2octyl ester and 4-(dimethylamino)-benzoic acid amyl ester;

esters of cinnamic acid, preferably 4-methoxycinnamic acid-2-ethylhexyl ester, 4-methoxycinnamic acid isopentyl ester, 2-cyano-3-phenylcinnamic acid-2-ethylhexyl ester (Octocrylene);

esters of salicylic acid, preferably salicylic acid-2-ethylhexyl ester, salicylic acid4-isopropylbenzyl ester, salicylic acid homomenthyl ester;

derivatives of benzophenone, preferably 2-hydroxy-4-methoxybenzo-phenone, 2-hydroxy4-methoxy4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4-tert.butylphenyl)-3-(4'-methoxyphenylypropane-1,3-dione;

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenone, preferably 2-hydroxy4-methoxybenzophenone-5-sulfonic acid and salts thereof; sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane- 1,3-dione or 1-phenyl-3-(4'-isopropylphenyl)-propane-1,3-dione. The UV-A and UV-B filters may of course also be used in the form of mixtures. Besides the soluble substances mentioned, insoluble pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Besides the two groups of primary UV filters mentioned above, secondary UV filters of the antioxidant type may also be used. Secondary UV filters of the antioxidant type interrupt the photochemical reaction chain which is initiated when UV rays penetrate into the skin. Typical examples are Superoxid-Dismustase, tocopherols (vitamin E) and ascorbic acid (vitamin C).

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formalde-hyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone.

Examples of perfume oils include the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (sandalwood, pockwood, cedarwood, rosewood), herbs and grasses (tarragon, lemon grass, sage, thyme), needles and, branches (spruce, fir, pine, dwarf pine), resins and balsams (galbanum, elemi, benzoin, myrrh, olibanum, opoponax). Animal raw materials, for example musk, civet and beaver, may also be used. Suitable synthetic and semisynthetic perfume oils are Ambroxan, eugenol, isoeugenol, citronellal, hydroxycitronellal, geraniol, citronellol, geranyl acetate, citral, ionone and methyl ionone.

Suitable dyes are any of the substances suitable and approved for cosmetic purposes as listed, for example, in the publication "Kosmetische Färbemittell" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be prepared by 15 standard cold or hot processes and are preferably produced by the phase inversion temperature method.

EXAMPLES

Production Example

In a 2-liter three-necked flask equipped with a stirrer, dropping funnel and distillation head, 540 g (2 moles) of partly hydrogenated tallow acid, 292 g (2 moles) of adipic acid and 2 g of sodium hypophosphite were mixed at 80° C. A vacuum of 20 mm Hg was applied and 596 g (4 moles) of triethanolamine were added in portions. The mixture was heated to 170° C., the pressure was reduced to 5 mm Hg and water was removed from the equilibrium until the acid value had fallen to below 5. 500 g of the resulting ester (corresponding to 1.5 equivalents) were transferred to a second flask and dissolved at 50° C. in 171 g of isopropyl alcohol. 180 g (1.43 moles) of dimethyl sulfate were slowly added to the mixture, followed by stirring for 5 hours at 65° C. A viscous, clear liquid with a cationic surfactant content of 1.2 meqlg and a dry residue of 80.5% by weight was obtained. A 5% by weight solution in water was clear and had a Gardner color standard number of 1. The product is commercially obtainable under the name of Dehyquart D 6003.

Application Examples

Seven detergent mixtures were prepared and tested for viscosity, stability in storage, solubility, dispersibility, soft ness and wet combability. Viscosity was measured in a Brookfield RVF viscosimeter (spindle 1, 10 r.p.m.) both immediately after production and after storage for 4 weeks at 40° C. Solubility was visually evaluated after production while dispersibility (i.e. the stability of the aqueous preparations) was visually evaluated after 1 h. Softness was determined by a panel of six experienced testers after forced application of the test mixtures to cotton fabric. On a scale of (1) to (4), (1) means very soft, (2) soft, (3) hard and (4) very hard. The results are expressed as the average values of the panel from three test cycles. In order to determine wet combability, the static charging between the fiber filaments is determined before and after treatment with the test solutions as a measure of combability. Mixtures 1 to 3 correspond to the invention while mixtures C1 to C4 are intended for comparison. The results are set out in Table 1.

TABLE 1

Composition and performance (pH = 3.1)

| | \multicolumn{7}{c}{Composition/performance} | | | | | | |
|---|---|---|---|---|---|---|---|
| | 1 | 2 | 3 | C1 | C2 | C3 | C4 |
| Dehyquart D 6003 | 2.5 | 1.25 | 3.75 | 5.0 | — | — | — |
| Dehyquart AU 46[1] | — | — | — | — | 5.0 | — | 2.5 |
| Rewopal V 3340[2] | 2.5 | 3.75 | 1.25 | — | — | 5.0 | 2.5 |
| Water | \multicolumn{7}{c}{to 100} | | | | | | |
| Viscosity [cps] | | | | | | | |
| immediately | 14 | 12 | 18 | 22 | 25 | 25 | 23 |
| after 4 w, 40° C. | 14 | 12 | 18 | 25 | 27 | 25 | 25 |
| Solubility | Clear | Clear | Clear | Clear | Cloudy | Cloudy | Cloudy |
| Dispersibility | Clear | Clear | Clear | Cloudy | Cloudy | Cloudy | Cloudy |
| Softness | 1.0 | 1.0 | 1.0 | 1.5 | 1.7 | 3.0 | 2.0 |
| Wet combability [mV] | | | | | | | |
| before | 64.2 | 59.0 | 61.2 | 60.5 | 61.1 | 60.8 | 59.9 |
| after | 20.1 | 18.7 | 21.3 | 30.0 | 31.1 | 59.3 | 44.7 |
| difference | 44.1 | 40.3 | 39.8 | 31.5 | 30.0 | 1.5 | 15.2 |

[1]Triethanolamine reacted with 2 moles of partly hydrogenated palm acid, methyl-quaternized, methosulfate salt
[2]Diethylenetriamine reacted with 2 moles of tallow acid, 7EO adduct.

What is claimed is:

1. A detergent mixture comprising (a) an oligomeric esterquat which is the product of the process which comprises reacting a mixture of a mono-carboxylic acid and a dicarboxylic acid with an alkanolamine to form an alkanolamine oligoester and reacting the alkanolamine oligoester with an alloiating agent and (b) the product of the process which comprises reacting an alkylene oxide and a fatty acid amidoamine, wherein the weight ratio of components (a) to (b) is from about 10:90 to about 90:10; and wherein the oligomeric esterquat has at least two cationic centers.

2. The detergent mixture of claim 1 wherein the carboxylic acids used to make the oligomeric esterquat have from about 6 to about 22 carbon atoms.

3. The detergent mixture of claim 2 wherein the dicarboxylic acid is adipic acid.

4. The detergent mixture of claim 1 wherein the mole ratio of the mono-carboxylic acids to the dicarboxylic acids in the oligomeric esterquat is from about 1:1 to about 3:1.

5. The detergent mixture of claim 1 wherein the alkanolamine is triethanolamine.

6. the detergent mixture of claim 1 wherein the molar ratio of the mixture of mono-carboxylic acid and a dicarboxylic acid to the alkanolamine is from about 1:1 to about 3:1.

7. The detergent mixture of claim 1 wherein component (a) is a compound of the formula (I):

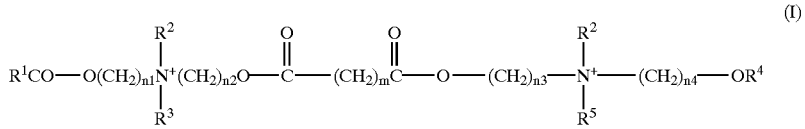

wherein $R^1CO$ is an aliphatic, linear or branched, saturated or unsaturated acyl group having from about 6 to about 22 carbon atoms, $R^2$ is an alkyl group having from 1 to 4 carbon atoms, each of $R^3$ and $R^5$ is an alkyl or hydroxyalkyl group having from 1 to 4 carbon atoms, $R^4$ is hydrogen or $R^1CO$ as defined above; each of n1, n2, n3 and n4 has a value of from 1 to 5 and m has a value of from 1 to 10.

8. The detergent mixture of claim 7 wherein $R^1CO$ is a linear saturated acyl group having from about 12 to about 18 carbon atoms, $R^2$ is a methyl group, $R^3$ and $R^5$ are each hydroxyethyl groups, $R^4$ is $R^1CO$ as defined above; each of n1, n2, n3 and n4 has a value of 2 and m has a value of 4.

9. The detergent mixture of claim 1 wherein component (b) is a compound of the formula (II):

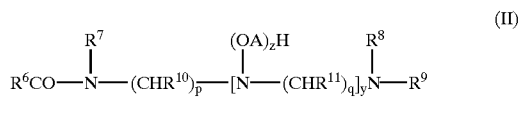

wherein $R^6CO$ is an aliphatic, linear or branched, saturated or unsaturated acyl group having from about 6 to about 22 carbon atoms; each of $R^7$ and $R^8$ is independently hydrogen or a hydroxy-substituted alkyl group having from 1 to 4 carbon atoms; $R^9$ is hydrogen, an alkyl group having from 1 to 4 carbon atoms or $R^6CO$ as defined above; each of $R^{10}$ and $R^{11}$ is hydrogen or a methyl group, A is a linear or branched alkylene group having from 2 to 4 carbon atoms, each of p and q has a value of from 1 to 3; y has a value of from 1 to 3 and z has a value of from 1 to 20.

10. The detergent mixture of claim 9 wherein component (b) is a compound of the formula (II) wherein $R^6CO$ is a linear saturated acyl group having from about 12 to about 18 carbon atoms; each of $R^7$, $R^8$, $R^{10}$ and $R^{11}$ is hydrogen; $R^9$ is $R^6CO$ as defined above; A is an ethylene group, p and q each have a value of 2, y has a value of 1 and z has a value of from 5 to 10.

11. The detergent mixture of claim 1 wherein component (a) is a compound of the formula (I):

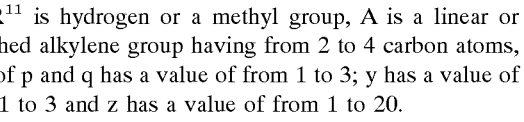

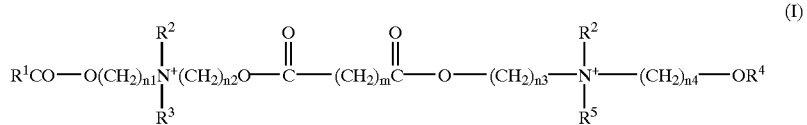

(I)

wherein $R^1CO$ is an aliphatic, linear or branched, saturated or unsaturated acyl group having from about 6 to about 22 carbon atoms, $R^2$ is an alkyl group having from 1 to 4 carbon atoms, each of $R^3$ and $R^5$ is an alkyl or hydroxyalkyl group having from 1 to 4 carbon atoms, $R^4$ is hydrogen or $R^1CO$ as defined above; each of n1, n2, n3 and n4 has a value of from 1 to 5 and m has a value of from 1 to 10, and component b) is a compound of the formula (II):

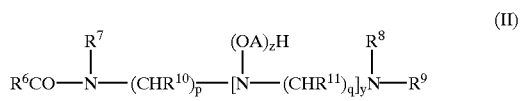

(II)

wherein $R^6CO$ is an aliphatic, linear or branched, saturated or unsaturated acyl group having from about 6 to about 22 carbon atoms; each of $R^7$ and $R^8$ is independently hydrogen or a hydroxy-substituted alkyl group having from 1 to 4 carbon atoms; $R^9$ is hydrogen, an alkyl group having from 1 to 4 carbon atoms or $R^6CO$ as defined above; each of $R^{10}$ and $R^{11}$ is hydrogen or a methyl group, A is a linear or branched alkylene group having from 2 to 4 carbon atoms, each of p and q has a value of from 1 to 3; y has a value of from 1 to 3 and z has a value of from 1 to 20.

12. The detergent mixture of claim 11 wherein in component a) $R^1CO$ is a linear saturated acyl group having from about 12 to about 18 carbon atoms, $R^2$ is a methyl group, $R^3$ and $R^5$ are each hydroxyethyl groups, $R^4$ is $R^1CO$ as defined above; each of ni, n2, n3 and n4 has a value of 2 and m has a value of 4; and wherein component (b) is a compound of the formula (II) wherein $R^6CO$ is a linear saturated acyl group having from about 12 to about 18 carbon atoms; each of $R^7$, $R^8$, $R^{10}$ and $R^{11}$ is hydrogen; $R^9$ is $R^6CO$ as defined above; A is an ethylene group, p and q each have a value of 2, y has a value of 1 and z has a value of fom 5 to 10.

* * * * *